(12) United States Patent
Sunada

(10) Patent No.: US 6,699,284 B2
(45) Date of Patent: Mar. 2, 2004

(54) INTRAOCULAR LENS

(75) Inventor: Tsutomu Sunada, Toyohashi (JP)

(73) Assignee: Nidek Co., Ltd., Gamagori (JP)

( * ) Notice: Subject to any disclaimer, the term of this patent is extended or adjusted under 35 U.S.C. 154(b) by 0 days.

(21) Appl. No.: 10/184,958

(22) Filed: Jul. 1, 2002

(65) Prior Publication Data

US 2003/0009216 A1 Jan. 9, 2003

(30) Foreign Application Priority Data

Jul. 9, 2001 (JP) ........................................ 2001-207643

(51) Int. Cl.[7] .................................................. A61F 2/16
(52) U.S. Cl. ...................................... 623/6.54; 623/6.42
(58) Field of Search ............................. 623/6.38, 6.39, 623/6.4–6.55

(56) References Cited

U.S. PATENT DOCUMENTS

| 5,071,432 A | 12/1991 | Baikoff |
| 5,628,796 A | 5/1997 | Suzuki |
| 6,485,516 B2 * | 11/2002 | Boehm ...................... 623/6.49 |

FOREIGN PATENT DOCUMENTS

| EP | 0 935 953 A2 | 8/1999 |
| JP | A 8-10274 | 1/1996 |
| WO | WO 97/27825 | 8/1997 |
| WO | WO 99/62434 | 12/1999 |
| WO | WO-99/62434 | * 12/1999 |
| WO | WO 00/66039 | 11/2000 |
| WO | WO 01/50984 A1 | 7/2001 |
| WO | WO-01/50984 | * 7/2001 |

* cited by examiner

*Primary Examiner*—Corrine McDermott
*Assistant Examiner*—Hieu Phan
(74) *Attorney, Agent, or Firm*—Oliff & Berridge, PLC

(57) ABSTRACT

An intraocular lens to be placed in an anterior chamber of a patient's eye is disclosed. The intraocular lens includes a lens part with a predetermined refractive power, including a front lens surface facing toward a cornea side and a back lens surface facing toward a fundus side when the intraocular lens is placed in the anterior chamber, a support part provided in an edge of the lens part and with an end positioned opposite to the edge, the end being insertable into an iris to penetrate to a fundus side thereof and back to a cornea side thereof to hold the lens part in the anterior chamber, and a hook provided in the end of the support part for preventing the support part from coming off the iris.

8 Claims, 4 Drawing Sheets

INTRAOCULAR LENS

BACKGROUND OF THE INVENTION

1. Field of the Invention

The present invention relates to an intraocular lens which is placed in an anterior chamber of a patient's eye.

2. Description of Related Art

There has been known an intraocular lens (anterior chamber intraocular lens) which is placed in an anterior chamber of a patient's eye for cataract treatment or refraction. As this type of intraocular lens to be placed in an anterior chamber, intraocular lenses shown in FIGS. 5A and 5B have been known. An intraocular lens 40 in FIG. 5A is constructed of a lens part (optical part) 41 having a predetermined refractive power and two support parts 42 extending from an edge of the lens part 41. An end of each support part 42 has a cut of a predetermined length to thereby pinch part of a peripheral area 21a which exerts no influence upon the motion of an iris 21, thereby holding the lens part 41 in the anterior chamber. On the other hand, an intraocular lens 50 in FIG. 5B is constructed of a lens part (optical part) 51 and four support parts 52 extending from an edge of the lens part 51. Each end of the support parts 52 is inserted to penetrate a peripheral area 21a of an iris 21 to hold the lens part 51 in the anterior chamber.

However, the intraocular lens 40 with the support parts 42 pinching the part 21a could not be securely held and may become detached from the iris 21. In the intraocular lens 50, each end of the support parts 52 penetrating the iris 21 is positioned on a fundus side of the iris 21. Accordingly, the ends of those support parts 52 may contact a crystalline lens in the case of a phakic eye.

SUMMARY OF THE INVENTION

The present invention has been made in view of the above circumstances and has an object to overcome the above problems and to provide an intraocular lens which is easy to place in an anterior chamber without becoming detached therefrom and includes an end of a support part that does not contact a crystalline lens of a phakic eye.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an intraocular lens to be placed in an anterior chamber of a patient's eye, including: a lens part with a predetermined refractive power, including a front lens surface facing toward a cornea side and a back lens surface facing toward a fundus side when the intraocular lens is placed in the anterior chamber; a support part provided in an edge of the lens part and with an end positioned opposite to the edge, the end being insertable into an iris to penetrate to a fundus side thereof and back to a cornea side thereof to hold the lens part in the anterior chamber; and a hook provided in the end of the support part for preventing the support part from coming off the iris.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

A detailed description of a preferred embodiment of an intraocular lens embodying the present invention will now be given referring to the accompanying drawings.

Figure 1A:
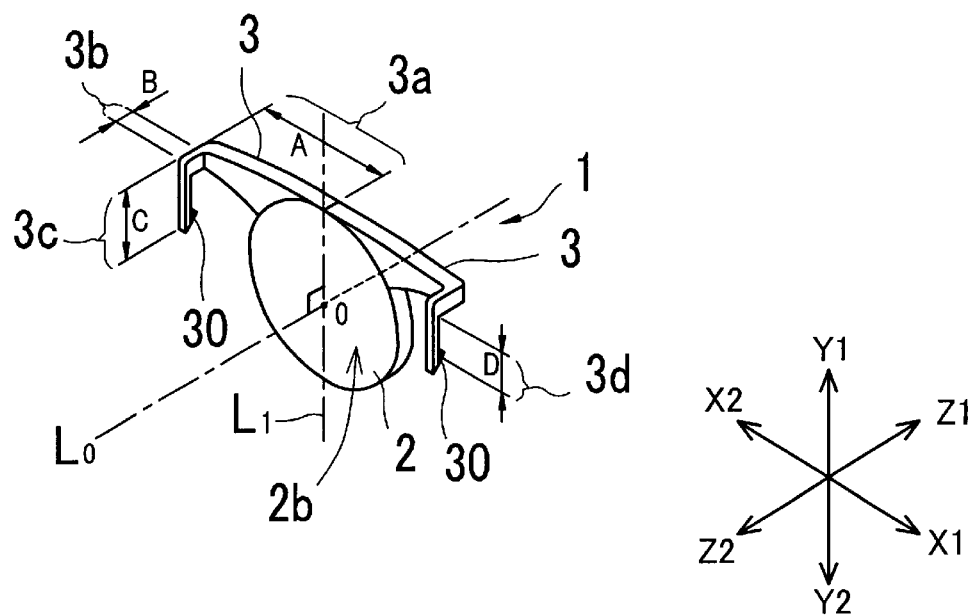
FIG. 1A is a schematic perspective view of an intraocular lens in an embodiment according to the invention.
Figure 1B:
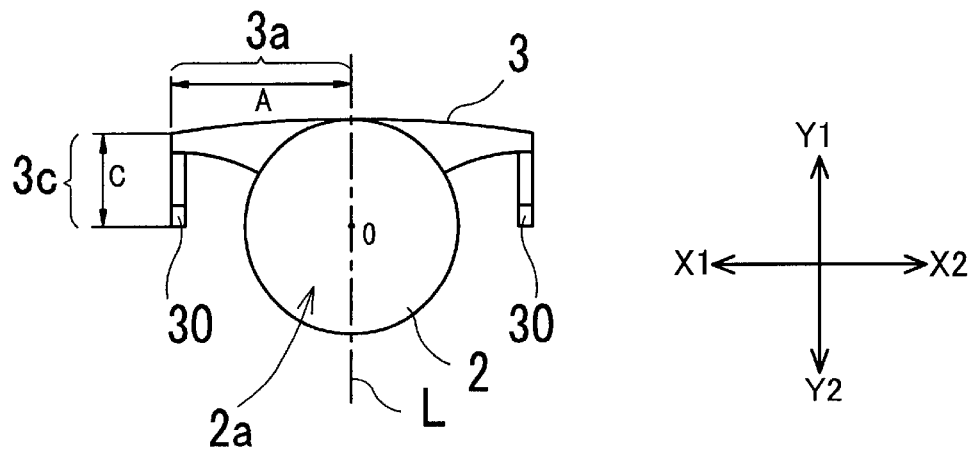
FIG. 1B is a front view of the intraocular lens of FIG. 1A.

FIG. 1A is a schematic perspective view of an intraocular lens in the present embodiment. FIG. 1B is a front view of FIG. 1A.

Numeral 1 is an intraocular lens constructed of a lens part (optical part) 2 having a predetermined refractive power and support parts 3 for securely holding the lens part 2 in an anterior chamber. The support parts 3 comprise two limbs extending from an edge (rim) of the lens part 2 in symmetric relation to an axis $L_1$ bisecting the lens part 2 as shown in FIGS. 1A and 1B. It is to be noted that, in the lens part 2 when placed in the anterior chamber, a surface facing a cornea is hereinafter referred to as a front lens surface 2a and the other surface facing a fundus is hereinafter referred to as a back lens surface 2b. The axis $L_1$ passes through a center O of the front lens surface 2a (the back lens surface 2b) in orthogonal relation to an optical axis $L_o$ of the lens part 2 passing through the center O.

A shape (structure) of the support parts 3 is explained in detail below. The two support parts 3 are of symmetrical configurations and thus one is mentioned below.

The support part 3 is provided with a first section 3a extending in a direction X1 (X2) (i.e. in a direction almost orthogonal to the axes $L_o$ and $L_1$) from the edge of the lens part 2 by a predetermined distance (a length A in FIG. 1A), a second section 3b bent at an almost right angle from an end of the first section 3a opposite to the lens part 2 to the back lens surface 2b side and extending in a direction Z2 almost parallel to the axis $L_o$ by a predetermined distance (a length B in FIG. 1B), and a third section 3c bent at an almost right angle from an end of the second section 3b opposite to the first section 3a to the center O side and extending in a direction Y2 almost parallel to the axis $L_1$ by a predetermined distance (a length C in FIG. 1A). Accordingly, as seen in FIG. 1B, the support part 3 is shaped like a letter L put into a sideways position.

An end of the third section 3c opposite to the second section 3b, that is, an end of the support part 3 (an extreme end in the present embodiment), is formed with a hook 30 for preventing detachment. To place the intraocular lens 1 in the anterior chamber, the end of the support part 3 is inserted in the iris to penetrate to a fundus side of the iris and back to a cornea side. At this time, the hook 30 is also inserted in the iris to the fundus side and then back to the cornea side, acting as a stopper for preventing the support part 3 from coming off. It is to be noted that the hook 30 is preferably arranged such that it is bent to the front lens surface 2a side in a direction Z1 almost parallel with the axis $L_o$.

The length A of the first section 3a corresponds to a length enough to put the extreme end of the support part 3, or the hook 30, in an area in which the support part 3 causes no motion failure of the iris when the lens part 2 is placed in a predetermined position of the anterior chamber (which is a position where the center O (the axis $L_o$) coincides with the center axis of a pupil of the patient's eye). The length B of the second section 3b corresponds to a length enough to prevent the back lens surface 2b from contacting the iris when the intraocular lens 1 is placed in the anterior chamber. It is to be noted that the first section 3a and the second section 3b may wholly be curved to prevent the back lens surface 2b from contacting the iris. The length C of the third section 3c is a length enough to be inserted in the iris. Similarly, the length D of a section 3d corresponding to a range excepting the hook 30 from the third section 3c, is a length enough to be inserted in the iris.

Furthermore, a maximum width of the intraocular lens 1 corresponding to a length (a linear distance) between the extreme end of one support part 3 and that of the other support part 3 is a length enough to place the extreme end (the hook 30) of each support part 3 in an area exerting no influence upon the motion of the iris when the intraocular lens 1 is put in place in the anterior chamber. The area which exerts no influence upon the motion of the iris corresponds to an area of the iris at a distance of 3.5 mm to 5 mm in radius from the pupil center of an adult's eye, which indicates an inert area.

Thus, the maximum width of the intraocular lens 1 is preferably determined such that a maximum radius of the intraocular lens 1 (which herein indicates one half of the linear distance between the extreme ends of the support parts 3) is about 3.5 mm to 5.0 mm from the center O. When the maximum radius exceeds 5.0 mm, an area of the iris in which the support parts 3 are inserted may be inflamed after placement of the intraocular lens 1 and the support parts 3 and operating tools may contact corneal endothelial cells during insertion of the support parts 3 in the iris, thus damaging the cells. When the maximum radius is lower than 3.5 mm, on the other hand, the support parts 3 may contact a moving (opening and closing) area of the iris, where the support parts 3 should not be inserted. Accordingly, the section 3d to be inserted in the iris is also preferably positioned at the maximum radius of 3.5 mm or more.

If the lens part 2 is made of a foldable material to allow insertion of the intraocular lens 1 with the lens part 2 folded into the anterior chamber, preferably, the support part 3 is arranged within half the circumference of a circular edge of the lens part 2 and the length C is designed to be shorter than the radius of the lens part 2 in order to make a minimum incision in the cornea. This is because, when the length C is longer than the radius of the lens part 2, it is necessary to make an incision of the size enough to insert the section 3c in the cornea although the lens part 2 is folded into about half the original size. The width and thickness of the support part 3 may be freely determined if only the support part 3 is able to hold the lens part 2 in the anterior chamber.

The material of the lens part 2 may be chosen from conventionally available materials; for example, polymethyl methacrylate (PPM), hydroxymethyl methacrylate (HEMA), a polymer of those materials, acrylic, silicone, or the like. The material of the support part 3 may be chosen from conventionally available materials having adequate elasticity and hardness; for example, the same material as that of the lens part 2, polypropylene, or the like.

The intraocular lens 1 may be made by integrally molding the lens part 2 and the support part 3 or by joining the lens part 2 and the support part 3 separately formed by conventionally known welding or adhesive polymerization.

The placing operation of the intraocular lens having the above structure will be explained below. Placing of the intraocular lens 1 in an anterior chamber of a phakic eye is herein exemplified with reference to FIGS. 2A to 2C.

Figure 2A:
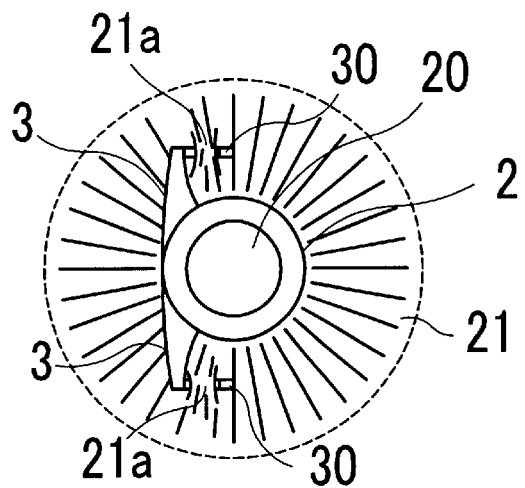
FIGS. 2A to 2C are views showing a state where the intraocular lens is attached to an iris.

An operator makes an incision in a cornea in a size just to insert (inject) the intraocular lens 1 and then insert the lens 1 into the anterior chamber. The operator adjusts the lens part 2 to a pupil 20 and picks up a peripheral area 21a which exerts no influence upon the motion of an iris 21 by use of a pair of tweezers. Each end of the support parts 3 is inserted laterally into this picked-up area 21a as shown in FIG. 2A.

Figure 2B:
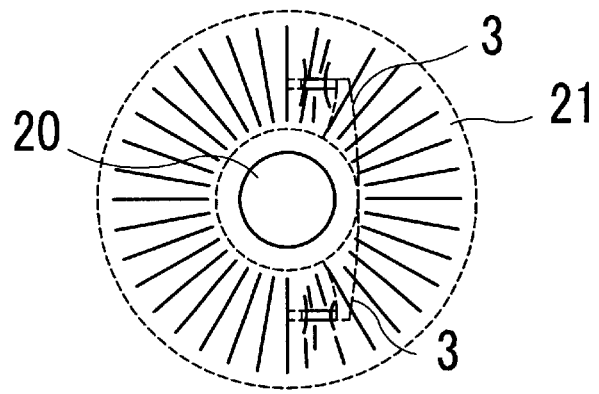

This state seen from a fundus side is shown in FIG. 2B. As shown in this figure, each end of the support parts 3 is inserted in the iris 21 so as to penetrate to its fundus side and back to its cornea side.

Figure 2C:
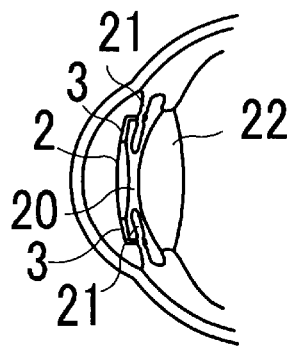

At this time, the hook 30 at each end of the support parts 3 prevents each end of the support parts 3 from coming off, so that the intraocular lens 1 can be placed in a predetermined position. As shown in FIGS. 2B and 2C, the extreme ends of the support parts 3 are positioned on the corneal side of the iris 21, which neither come into contact with the crystalline lens 22 nor damage it. The third sections 3c (the sections 3d) are in direct contact with the iris 21, which makes it possible to stably place the intraocular lens 1 in the anterior chamber.

It is to be noted that piercing of the peripheral area 21a may be performed by previously picking up the peripheral area 21a and penetrating by use of a surgical tool or the like.

In the embodiment, the end of the support part 3 of the intraocular lens 1 is inserted into the peripheral area 21a in a lateral direction, but it is not limited thereto. It may be turned 90 degrees to be inserted in a vertical direction.

Figures 4A, 4B:
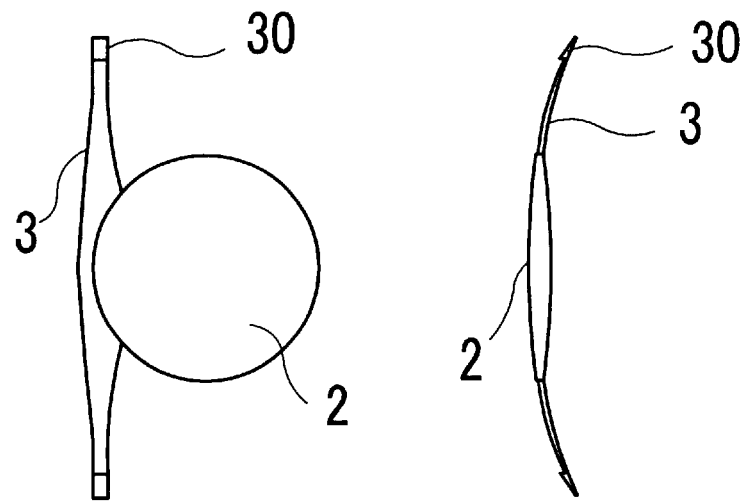
FIG. 4A is a front view of an intraocular lens in a modification of the embodiment.
FIG. 4B is a side view of the intraocular lens of FIG. 4A.
Figure 5A:
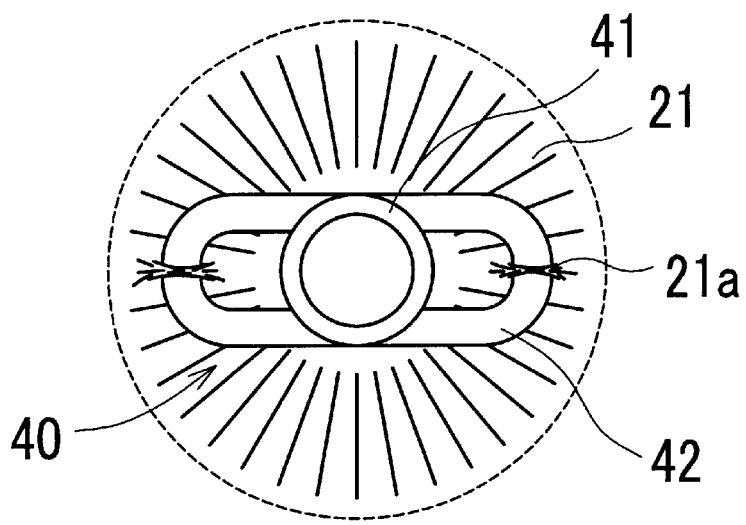
FIGS. 5A and 5B are views showing intraocular lenses of the type to be placed in anterior chambers in prior arts.
Figure 5B:
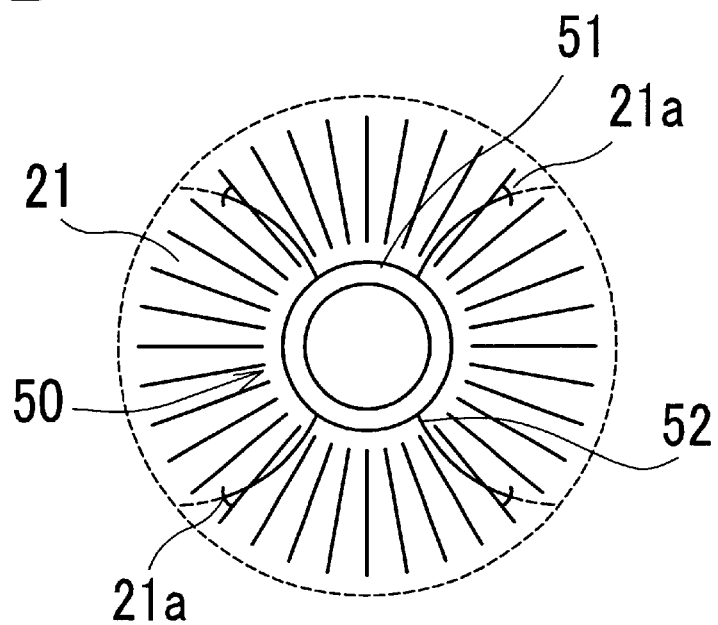

Each support part 3 substantially has an L-shape in the embodiment, but it is not limited thereto. The support parts 3 may have any shape if only has, at the end, the hook 30 for preventing the support parts 3 from coming off and can hold the lens part 2 in the anterior chamber. For instance, as shown in FIGS. 4A and 4B, an intraocular lens having support parts 3 linearly extending from an edge of a lens part 2 and curved for preventing the lens part 2 from contacting the iris. In this case, preferably, each support part 3 is provided with a hook 30 at an end and a maximum radius of the intraocular lens is from about 3.5 mm to about 5.0 mm from the center O. It is preferable that the portion to be inserted in the iris is positioned at the maximum radius of 3.5 mm or more.

In the support parts 3 shown in FIG. 1A, the third sections 3c may be formed extending in directions X1 and X2 respectively.

Furthermore, when the diameter of the lens part 2 is longer than the length C of the end of the support part 3 as with the intraocular lens (in FIG. 1) in the present embodiment, a smaller incision can be made in the cornea for insertion of the intraocular lens 1.

Figure 3:
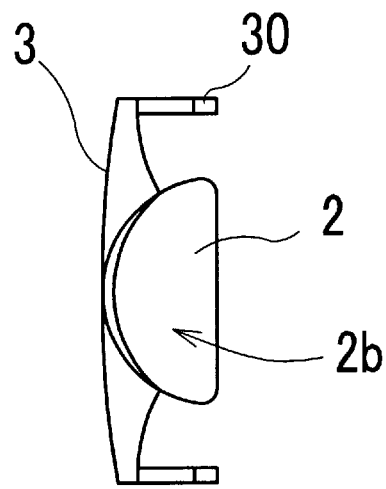
FIG. 3 is a view of the intraocular lens of FIG. 1A in a state where a lens part is folded.

When the lens part 2 is folded in advance as shown in FIG. 3, the size of an incision is sufficient if only it is at most equal to the length C of the ends of the support parts 3. More preferably, as mentioned above, the length C is shorter than the radius of the lens part 2.

As described above, according to the present invention, the intraocular lens can be easily placed in the anterior chamber without coming off, and the ends of the support parts can be prevented from contacting the crystalline lens even in a phakic eye.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An intraocular lens to be placed in an anterior chamber of a patient's eye, including:

a lens part with a predetermined refractive power, including a front lens surface facing toward a cornea side and a back lens surface facing toward a fundus side when the intraocular lens is placed in the anterior chamber;

a support part provided in and extending from an edge of the lens part and provided with an end positioned opposite to the edge of the lens part, the support part serving to hold the lens part in the anterior chamber so as to prevent the back lens surface from contacting an iris of the eye, the end being insertable into the iris to fix the support part to the iris; and a hook provided in the end of the support part, for preventing the support part from coming off the iris, the hook being formed in a barb-like shape having a thickness that increases from an edge of the end and sharply decreases at a distance from the edge.

2. The intraocular lens according to claim 1, wherein a maximum radius of the intraocular lens from a center of the front lens surface is 3.5 mm to 5.0 mm.

3. The intraocular lens according to claim 1, wherein the support part includes at least two support parts provided symmetrically to an axis passing through a center of the front lens surface.

4. The intraocular lens according to claim 1, wherein the lens part is made of a foldable material, and the support part includes two support parts provided within half a circumference of the edge of the lens part.

5. The intraocular lens according to claim 1, wherein the support part has a section bent to the back lens surface side in a direction almost parallel to an optical axis of the lens part.

6. The intraocular lens according to claim 1, wherein the lens part is made of a foldable material.

7. The intraocular lens according to claim 1, wherein the support part has a first section to be positioned in the cornea side of the iris, a second section to be positioned in the fundus side of the iris and a third section to be positioned in the cornea side of the iris when the support part is fixed to the iris, the first section provided in and extending from the edge of the lens part, the second section provided between the first section and the third section, the end provided in the third section.

8. The intraocular lens according to claim 1, wherein the support part is curved so as to prevent the back lens surface from contacting the iris.

* * * * *